United States Patent [19]

Bingham

[11] 4,367,227

[45] Jan. 4, 1983

[54] METHOD AND COSMETIC COMPOSITION FOR REDUCING SEBUM SECRETION

[75] Inventor: Keith D. Bingham, Shepperton, England

[73] Assignee: Lever Brothers Company, New York, N.Y.

[21] Appl. No.: 973,493

[22] Filed: Dec. 26, 1978

Related U.S. Application Data

[63] Continuation of Ser. No. 775,187, Mar. 7, 1977, abandoned.

[30] Foreign Application Priority Data

Mar. 11, 1976 [GB] United Kingdom ................ 9800/76

[51] Int. Cl.$^3$ .............................................. A61K 31/56
[52] U.S. Cl. .............................. 424/243; 424/DIG. 4; 424/47; 424/362
[58] Field of Search ......................... 424/243, DIG. 4

[56] References Cited

U.S. PATENT DOCUMENTS

| 3,234,093 | 2/1966 | Wechert | 424/243 |
| 3,287,222 | 11/1966 | Larde et al. | 424/28 |
| 3,577,516 | 5/1971 | Gould et al. | 424/28 X |
| 3,632,740 | 1/1972 | Robinson et al. | 424/28 |
| 3,806,593 | 4/1974 | Swanbeck et al. | 424/28 |
| 3,896,807 | 7/1975 | Buchalter | 424/28 X |
| 4,039,669 | 8/1977 | Beyler et al. | 424/243 |

FOREIGN PATENT DOCUMENTS

| 726674 | 1/1966 | Canada | 424/243 |
| 1408036 | 10/1975 | United Kingdom . | |

OTHER PUBLICATIONS

Chem. Abst. I–vol. 72, 28627, (1970).
Chem. Abst. II–vol. 72, 75091a, (1970).
Chem. Abst. III–vol. 73, 32068b, (1970).

*Primary Examiner*—Dale R. Ore
*Attorney, Agent, or Firm*—James J. Farrell

[57] ABSTRACT

A cosmetic composition for reducing sebum secretion comprising in solution in a $C_2$-$C_3$ aliphatic alcohol an effective amount of cyproterone acetate.

13 Claims, No Drawings

METHOD AND COSMETIC COMPOSITION FOR REDUCING SEBUM SECRETION

This is a continuation of application Ser. No. 775,187, filed Mar. 7, 1977, now abandoned.

This invention relates to cosmetics and in particular to cosmetic compositions for applying to the skin to inhibit sebum excretion.

In the British Journal of Dermatology (1976) 95, 427 there are reported unsuccessful attempts to inhibit sebum excretion by applying cyproterone acetate to the skin. The prior experiments reported involved applying cyproterone acetate in a base consisting of in one case a dimethyl sulphoxide water mixture and in another case Cetomacrogol cream (BPC (Formula A).

We have now discovered that a cosmetic composition consisting of a solution of cyproterone acetate in a $C_2$–$C_3$ *aliphatic alcohol is effective to reduce sebum excretion when applied to the skin.*

According therefore to one aspect of the present invention there is provided a cosmetic composition comprising a solution of cyproterone acetate in a $C_2$–$C_3$ aliphatic alcohol, preferably ethanol.

In order to facilitate application of the solution to the skin it preferably comprises a thickening agent. While any suitable thickening agent which forms a viscous or gelled solution may be used, we prefer to use a hydroxypropylcellulose thickener, for example the material sold under the trade name KLUCEL. Suitable amounts are from about 0.5 to about 5% by weight.

Other common additives for cosmetic compositions may also be included, particularly perfume and/or a colouring agent. The composition may also include a proportion of water, but the amount used should allow the cyproterone acetate to remain dissolved in the composition.

The concentration of the cyproterone acetate in the alcoholic solution is suitably 0.01 to 10%. Other concentrations may be used. Generally speaking, more concentrated solution can be employed when the intended frequency of application to the skin is less.

The invention also relates to the combination of the above cosmetic composition and an applicator for applying the composition to the skin. The applicator may be, for example, an absorbent pad, a roll-on applicator or a spray applicator such as a pump or aerosol spray applicator.

The invention also relates to a method of treating skin to reduce sebum excretion by applying thereto a cosmetic composition as described above.

The following examples of cosmetic compositions illustrate the invention. Percentages are by weight.

EXAMPLE 1

|  | % |
|---|---|
| Cyproterone acetate | 0.2 |
| Ethanol | 99.8 |

EXAMPLE 2

The following cosmetic composition is suitable for applying from a roll-on applicator.

|  | % |
|---|---|
| Cyproterone acetate | 0.5 |
| Hydroxypropylcellulose | 1.0 |
| Perfume | 0.1 |
| Colour | qs |
| Ethanol | to 100.0 |

The inhibition of sebum excretion by cyproterone acetate in an alcoholic base was demonstrated by the following experiment.

In this experiment a measure of the sebum excretion from bald areas of subjects exhibiting male pattern baldness was determined. Before treatment with cyproterone acetate, measurements were taken of the sebum excretion in the following manner. First of all, in order to remove sebum from the areas to be treated a number of strips of degreased Velin tissue were held in position on the bald area of the subject for 10 minutes and this was repeated twice. One and a half hours later a glass cube having a ground surface (1.2 cm$^2$) was placed with this surface in contact with the treatment area for 0.5 minutes. The cube was attached to a CORREX gauge in order that the same pressure (about 80–100 g) was applied in each case. In order to remove the sebum from the glass cube the latter was submerged in 10 mls distilled diethyl ether for 10 minutes and in another 10 mls of distilled diethyl ether of 5 minutes. The combined ether extracts were evaporated under nitrogen. The amount of sebum was determined by adding to the sebum 3 mls of concentrated sulphuric acid and heating the mixture in an oven at 180°–200° C. for 45 minutes. To the cooled charred product 3 mls of distilled water were added with thorough mixing. The density of the solution obtained was then measured using a UNICAM SP 500 spectrophotometer at 375 nm against a water blank. From a standard curve the amount of sebum in the solution was determined. In the table given below the sebum excretion value is the amount of sebum removed from the scalp of the subject expressed as $\mu g/cm^2$.

This determination of sebum excretion on the subject prior to treatment was repeated two or three times and the value in the table below is the mean value.

Thereafter treatment with the solution of Example 1 was commenced with daily applications (five days of the week) of 1 ml to an area of approximately 25 cm$^2$.

Measurements of sebum excretion were made in the above manner after 2 and 3 months of treatment. Two or three determinations (depending on the availability of the subjects) were made on consecutive days and the mean values are given in the table below which gives the results obtained. A dash means that no determination was made.

| | Sebum Excretion Value | | |
|---|---|---|---|
| Subject | Before Start of Treatment | After 2 Months' Treatment | After 3 Months' Treatment |
| 1 | 69.3 | — | 66.1 |
| 2 | 74.0 | — | 32.1 |
| 3 | 99.9 | — | 73.6 |
| 4 | 79.6 | — | 34.1 |
| 5 | 95.5 | — | 52.6 |
| 6 | 84.6 | 64.7 | 34.0 |
| 7 | 181.0 | 64.5 | — |
| 8 | 91.3 | 66.0 | 36.3 |
| 9 | 112.0 | 88.4 | 51.8 |
| 10 | 73.1 | 51.2 | 24.4 |

-continued

| | Sebum Excretion Value | | |
|---|---|---|---|
| Subject | Before Start of Treatment | After 2 Months' Treatment | After 3 Months' Treatment |
| 11 | 105.6 | 68.3 | 33.8 |
| 12 | 49.4 | 46.5 | 19.4 |

What is claimed is:

1. A topical cosmetic composition for reducing sebum excretion consisting essentially of:
   (a) an amount effect to reduce sebum excretion of cyproterone acetate; and
   (b) a $C_2$ to $C_3$ aliphatic alcohol or a mixture of a $C_2$ to $C_3$ aliphatic alcohol and water.

2. A topical cosmetic composition according to claim 1 further consisting of a thickening agent, wherein said thickening agent is present in an amount sufficient to render said composition a viscous or gelled solution.

3. A topical cosmetic composition according to claim 1, wherein said cyproterone acetate is present in said composition at a level of about 0.01 to about 10 percent by weight of said composition.

4. A topical cosmetic composition according to claim 3, wherein said aliphatic alcohol is ethanol.

5. A topical cosmetic composition according to claim 2, wherein,
   (a) said cyproterone acetate is present in said composition at a level of about 0.01 to about 10 percent by weight of said composition; and
   (b) said thickening agent is present in said composition at a level of about 0.5 to about 5 percent by weight of said composition.

6. A topical cosmetic composition according to claim 5, wherein said thickening agent is a hydroxypropylcellulose.

7. A topical cosmetic composition for reducing sebum excretion consisting of:
   (a) about 0.01 to about 10 percent by weight of said composition of cyproterone acetate;
   (b) about 0.5 to about 5 percent by weight of a thickening agent;
   (c) a $C_2$ to $C_3$ aliphatic alcohol or a mixture of a $C_2$ to $C_3$ aliphatic alcohol and water; and
   (d) a physiologically acceptable cosmetic additive selected from the group consisting of perfume, coloring agents, and mixtures thereof.

8. A method of inhibiting sebum excretion comprising applying to the skin an effective amount of a composition wherein said composition comprises:
   (a) an amount effective to reduce sebum excretion of cyproterone acetate, and
   (b) a $C_2$ to $C_3$ aliphatic alcohol.

9. A method according to claim 8 wherein said composition further comprises a thickening agent wherein said thickening agent is present in an amount to render said composition a viscous or gelled solution.

10. A method according to claim 8 wherein said cyproterone acetate is present in said composition at a level of about 0.01 to about 10 percent by weight of said composition.

11. A method according to claim 9 wherein:
    (a) said cyproterone acetate is present in said composition at a level of about 0.01 to about 10 percent by weight of said composition; and
    (b) said thickening agent is present in said composition at a level of about 0.5 to about 5 percent by weight of said composition.

12. A method according to claim 11 wherein said thickening agent is hydroxypropylcellulose.

13. A cosmetic device for reducing sebum excretion comprising:
    (a) a cosmetic composition comprising: (i) an amount effective to reduce sebum excretion of cyproterone acetate; and (ii) a $C_2$ to $C_3$ aliphatic alcohol; and
    (b) an applicator in combination with said composition wherein said applicator is selected from the group consisting of:
       (i) an absorbent pad,
       (ii) a roll-on applicator,
       (iii) a pump spray applicator, and
       (iv) an aerosol spray applicator;
    wherein said combination provides a means for applying said composition to the skin.

* * * * *